United States Patent
Stoval, III et al.

(10) Patent No.: US 7,518,619 B2
(45) Date of Patent: Apr. 14, 2009

(54) METHOD AND APPARATUS FOR INTEGRATING THREE-DIMENSIONAL AND TWO-DIMENSIONAL MONITORS WITH MEDICAL DIAGNOSTIC IMAGING WORKSTATIONS

(75) Inventors: William Murray Stoval, III, Draper, UT (US); Murali Kumaran Kariathungal, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 402 days.

(21) Appl. No.: 11/268,190

(22) Filed: Nov. 7, 2005

(65) Prior Publication Data

US 2007/0103459 A1    May 10, 2007

(51) Int. Cl.
G09G 5/00    (2006.01)
(52) U.S. Cl. .................................. 345/619; 382/128
(58) Field of Classification Search ................. 345/619; 382/128, 131, 132, 154
See application file for complete search history.

(56) References Cited

U.S. PATENT DOCUMENTS

| | | | | | |
|---|---|---|---|---|---|
| 4,259,725 | A | * | 3/1981 | Andrews et al. | ............ 715/856 |
| 4,881,068 | A | * | 11/1989 | Korevaar et al. | ............... 345/6 |
| 5,954,650 | A | * | 9/1999 | Saito et al. | .................. 600/425 |
| 6,236,742 | B1 | * | 5/2001 | Handel | ........................ 382/128 |
| 6,799,066 | B2 | * | 9/2004 | Steines et al. | ............... 600/407 |
| 7,206,462 | B1 | * | 4/2007 | Betke et al. | .................. 382/280 |
| 2002/0164062 | A1 | * | 11/2002 | Newman | ..................... 382/132 |
| 2003/0185426 | A1 | * | 10/2003 | Ohishi | ........................ 382/128 |
| 2004/0092815 | A1 | * | 5/2004 | Schweikard et al. | ......... 600/425 |
| 2004/0153128 | A1 | * | 8/2004 | Suresh et al. | .................. 607/14 |
| 2005/0041843 | A1 | * | 2/2005 | Sawyer | ........................ 382/128 |
| 2005/0111714 | A1 | * | 5/2005 | Shen et al. | ................... 382/128 |
| 2005/0111757 | A1 | * | 5/2005 | Brackett et al. | .............. 382/294 |
| 2006/0204064 | A1 | * | 9/2006 | Hay | ............................ 382/128 |

(Continued)

OTHER PUBLICATIONS

Gregg Favalora and Cameron Lewis, "Spatial 3D: The End of Flat-Screen Thinking," Actuality Systems, Inc.—Jul. 2003 www.actuality-systems.com.

(Continued)

*Primary Examiner*—Kee M Tung
*Assistant Examiner*—David H Chu
(74) *Attorney, Agent, or Firm*—McAndrews, Held & Malloy, Ltd.; Peter J. Vogel; Michael A. Dellapenna

(57) ABSTRACT

A system and method for utilizing a spatial three-dimensional display unit with a medical diagnostic imaging system is disclosed. The medical diagnostic imaging system may be a picture archival communication system. The system may include at least one two-dimensional display unit and an additional spatial three-dimensional display unit. Accordingly a user may view two and three-dimensional images of similar anatomical objects. The two and three-dimensional images may be linked, providing the user with a consistent viewing angle. The system may be used to review a surgical path. The display parameters of a first three-dimensional data set may be mapped to a second three-dimensional data set. The surgical path of the first data set and the second data set may be displayed on spatial display units. Accordingly, the anatomical objects along the surgical path may be viewed at different points in time, for example prior to surgery and after surgery.

12 Claims, 4 Drawing Sheets

U.S. PATENT DOCUMENTS

2007/0019849 A1* 1/2007 Kaufman et al. ............ 382/128
2007/0110289 A1* 5/2007 Fu et al. .................... 382/128
2007/0177780 A1* 8/2007 Chui ......................... 382/128
2007/0225587 A1* 9/2007 Burnell et al. .............. 600/407
2007/0259966 A1* 11/2007 Cagnoni et al. ............. 514/716
2007/0274582 A1* 11/2007 Yatziv et al. ............... 382/131

OTHER PUBLICATIONS

Won S. Chun, Actuality Systems, Inc., "Perspecta® Spatial 3D System SDK Manual"—Aug. 23, 2004 www.actuality.systems.com.
Medical News Today, "Exploring Cutting-Edge 3D Imaging System for Cancer Treatment Planning, Rush University Medical Center"—Apr. 29, 2005. http://www.medicalnewstoday.com/medicalnews.php?newsid=23565#.

* cited by examiner

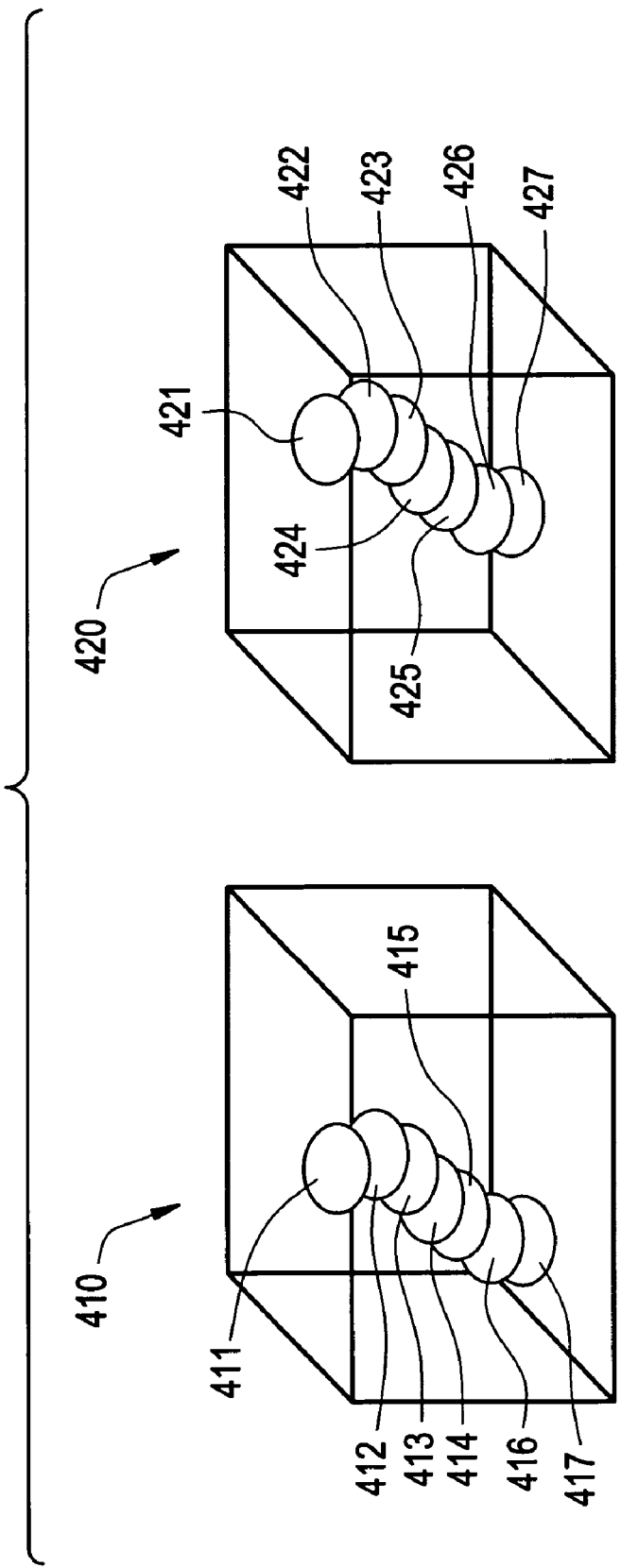

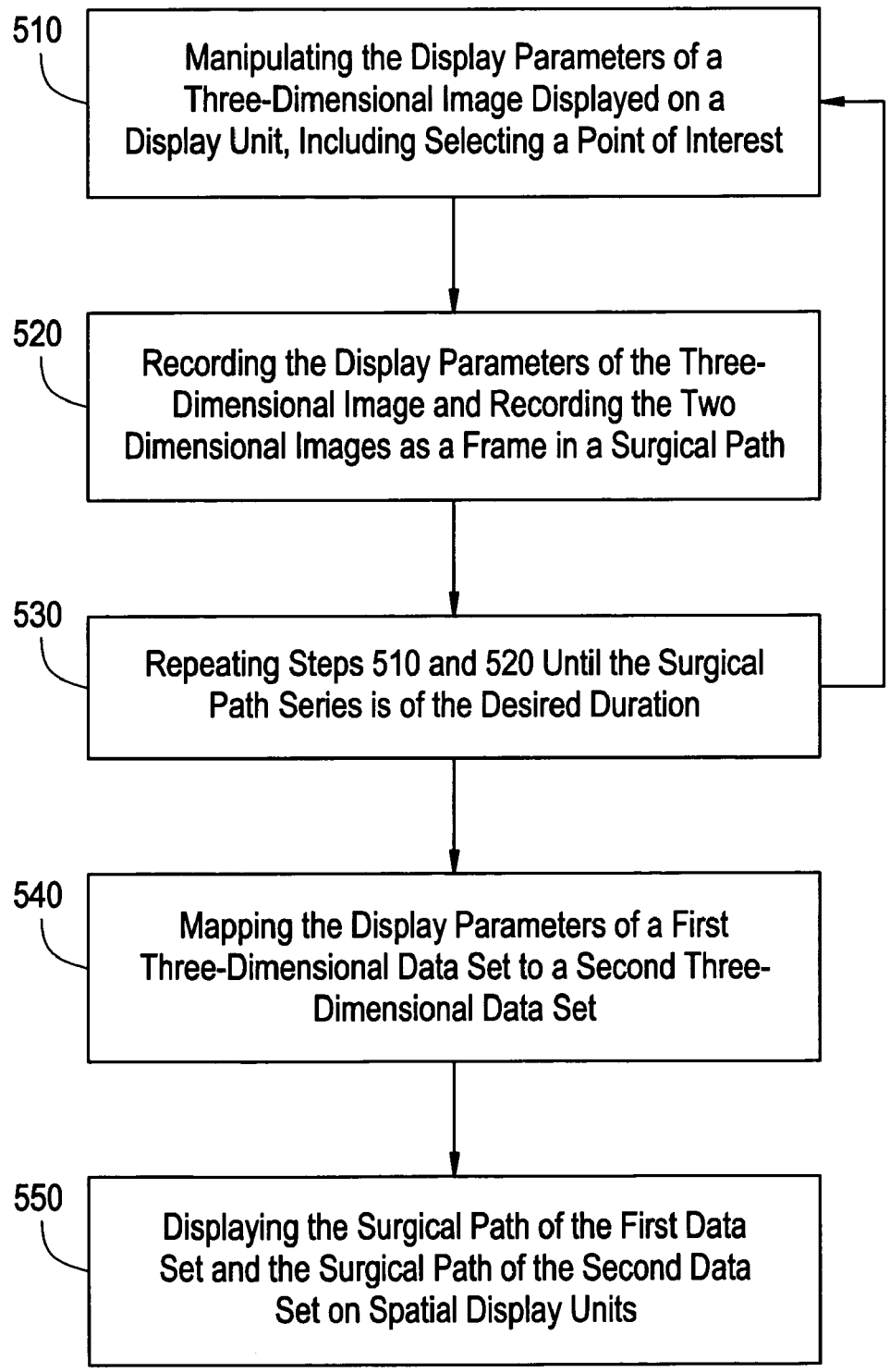

METHOD AND APPARATUS FOR INTEGRATING THREE-DIMENSIONAL AND TWO-DIMENSIONAL MONITORS WITH MEDICAL DIAGNOSTIC IMAGING WORKSTATIONS

BACKGROUND OF THE INVENTION

The present invention generally relates to a system and method for improved medical imaging. Particularly, the present invention relates to a more efficient system and method for configuring and interpreting medical images.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient, for example. The generated images may be used for many purposes. For instance, internal defects in an object may be detected. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

An example of a medical diagnostic imaging system is Picture Archival Communication Systems (PACS). PACS is a term for equipment and software that permits images, such as x-rays, ultrasound, CT, MRI, EBT, MR, or nuclear medicine for example, to be electronically acquired, stored and transmitted for viewing. Images from an exam may be viewed immediately or stored, or transmitted. The images may be viewed on diagnostic workstations by users, for example radiologists. In addition to viewing the images, the user may also view patient information associated with the image for example the name of the patient or the patient's sex.

The data acquired for a PACS system are generally two-dimensional. The two-dimensional data is generally viewed by a user, however, as a series of two-dimensional images. A user may view two-dimensional "slices" of a patient's anatomy. The user may then attempt to mentally reconstruct a three-dimensional model of the patient's anatomy. As each patient is different, the effort to read and understand the two-dimensional data may be time consuming and substantial.

As computer and medical imaging technology has become more sophisticated, PACS diagnostic workstations have become capable of displaying a three-dimensional projection of the medical images. Typically, the display of the three-dimensional medical images is displayed in a similar manner as the two-dimensional images. Additionally, the display of the three-dimensional medical images may be displayed on a similar type of flat two-dimensional capable monitors as the two-dimensional images. The two-dimensional projection of the three-dimensional data of a patient's anatomy may permit a user to rotate, flip, and perform other operations on the image to facilitate the display of data for the user. These types of three-dimensional displays of information are not truly three-dimensional, however, as they are displayed on two-dimensional flat screens. Accordingly, the projection of three-dimensional images onto two-dimensional displays limit the ability of the user to fully utilize the data collected about a patient's anatomy.

In an effort to better utilize three-dimensional data of all sorts, products are being developed to display three-dimensional data as true three-dimensional models on three-dimensional display units (three-dimensional monitors, not stereoscopic monitors), as opposed to three-dimensional data projected on two-dimensional display units. Three-dimensional display units are different than flat-screen 3D as three-dimensional display units offer three-dimensional imagery that truly occupies a volume of space. Such three-dimensional display units display spatial 3D as opposed to flat-screen 3D. As an example, one of the spatial display units currently being developed is the Perspecta™ 3D System by Actuality Systems, Inc. of 213 Burlington Road, Bedford, Mass. 01730, http://www.actuality-systems.com.

Current spatial display units are capable of displaying many types of three-dimensional data. One type of data that may be displayed on spatial display units is three-dimensional medical data. The display of three-dimensional medical data on spatial display units, however, is generally performed independently of other tools available to a doctor or radiologist. Accordingly, a user may utilize a spatial display unit to view three-dimensional medical data, but the user is isolated from other tools that may aide in diagnosis and treatment. A user's workflow may therefore be hampered and unnecessarily time consuming. Therefore, a need exists for a system and method that provides for a relationship between a spatial display unit and other tools available to a physician or radiologist. Such a system and method may allow a user to be more efficient and effective in diagnosing and treating medical conditions.

SUMMARY OF THE INVENTION

Certain embodiments of the present invention include a medical diagnostic imaging system. The medical diagnostic imaging system includes a computer unit for manipulating three-dimensional data. The computer unit has computer software operating a display protocol for configuring three-dimensional data for display. The medical diagnostic imaging system also includes at least a first spatial three-dimensional display unit for displaying a first three-dimensional data set. The medical diagnostic imaging system may be a picture archival communication system. Additionally, the system may include a second spatial three-dimensional display unit for displaying a second three-dimensional data set. The first three-dimensional data set may be linked to the second three-dimensional data set. The system may also include a first two-dimensional display unit for displaying at least one two-dimensional data set. The first thee-dimensional data set and the first two-dimensional data set may be linked.

The system may include a first two-dimensional display unit for displaying one two-dimensional data set, a second two-dimensional display unit for displaying one two-dimensional data set, and a third two-dimensional display unit for displaying one two-dimensional data set. The first two-dimensional data set may correspond to an axial view. The second two-dimensional data set may correspond to a sagittal view. The third two-dimensional data set may correspond to a coronal view for a selected point of interest.

Certain embodiments of the present invention may include a method for using medical images to review a surgical path. The method includes manipulating the display parameters of a first three-dimensional data set displayed on a spatial display unit. Next, recording the display parameters of said first three-dimensional data set, and recording the corresponding two-dimensional images, as a frame in a surgical path. Next, the method includes repeating the above steps of manipulating and recording until the surgical path is of the desired duration. The desired duration may be determined by a user. Next, mapping the display parameters of the first three-dimensional data set to a second three-dimensional data set. Finally, displaying the surgical path of the first data set and the surgical path of the second data on spatial display units.

The surgical path of the first data set may be linked to the surgical path of the second data set. An axial, sagittal, and coronal view may be recorded for each frame and may be recorded for the point of interest for each frame. Additionally, an oblique view is recorded for each frame. The first data set may be a historical data set and the second data set may be a current data set.

Certain embodiments of the present invention may include a computer-readable storage medium that includes a set of instructions for a computer. The set of instructions for a computer may include a manipulation routine for manipulating the display parameters of a first three-dimensional data set displayed on a spatial display unit. The set of instructions may also include a recordation routine for recording the display parameters of the first three-dimensional data set, and recording the corresponding two-dimensional images, as a frame in a surgical path. The set of instructions may also include a repeat routine for repeating the above steps of manipulating and recording until the surgical path is of the desired duration. The desired duration of the surgical path may be determined by a user. The set of instructions may also include a mapping routine for mapping the display parameters of the first three-dimensional data set to a second three-dimensional data set. The set of instructions may also include a display routine for displaying the surgical path of the first data set and the surgical path of the second data on spatial display units.

With reference to the computer instructions above, the surgical path of the first data set may be linked to the surgical path of the second data set. Moreover, an axial, sagittal, and coronal view may be recorded for each frame and may be recorded for the point of interest for each frame. Additionally, an oblique view may be recorded for each frame. The first data set may be a historical data set and the second data set may be a current data set.

BRIEF DESCRIPTION OF THE DRAWINGS

FIG. 4 illustrates as an embodiment of the present invention an application of planning and reviewing a surgical path.

FIG. 5 illustrates a method for utilizing two and three dimensional images to review a surgical path in accordance with an embodiment of the present invention.

DETAILED DESCRIPTION OF THE INVENTION

Figure 1:
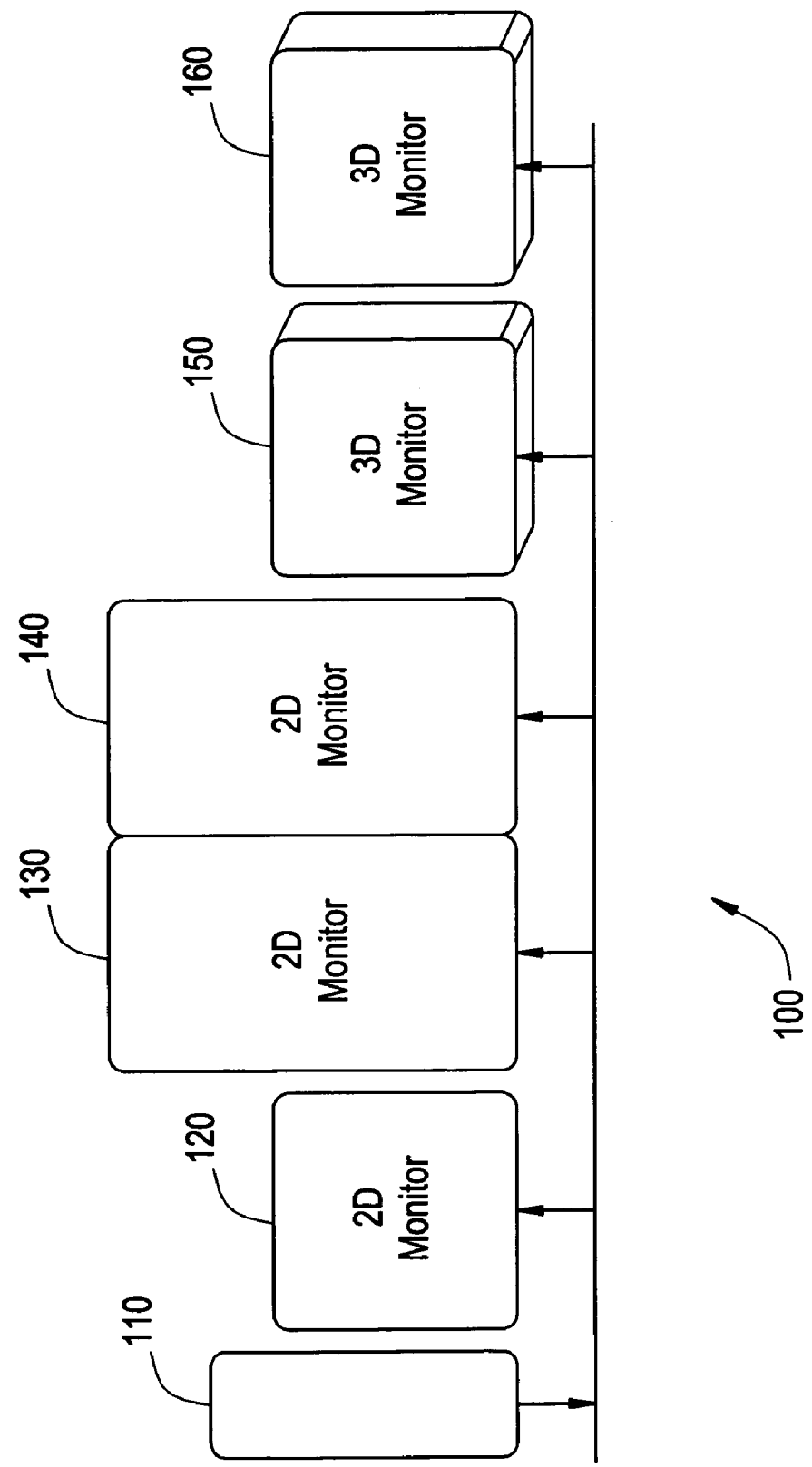
FIG. 1 illustrates an example of a system that may be used in accordance with an embodiment of the present invention.

FIG. 1 illustrates a system 100 for controlling the display and synchronization of three-dimensional data with other three-dimensional data and three-dimensional data with two-dimensional data. The system 100 includes a computer unit 110. The computer unit 110 may be any equipment or software that permits electronic medical images, such as x-rays, ultrasound, CT, MRI, EBT, MR, or nuclear medicine for example, to be electronically acquired, stored, or transmitted for viewing and operation. The computer unit 110 may receive input from a user. The computer unit 110 may be connected to other devices as part of an electronic network. In an embodiment, the computer unit 110 may be, or may be part of, a picture archival communication system (PACS).

The system 100 also includes five display units, 120, 130, 140, 150, and 160. In an embodiment, the display units 120, 130, and 140 are two-dimensional flat panel display units. Display units 150 and 160 are three-dimensional spatial display units. An example of display units 150 and 160 that may be used in accordance with an embodiment of the present invention is the Perspecta™ 3D System by Actuality Systems, Inc. as discussed above. Although five display units are shown in the embodiment of FIG. 1, any number of display units may be used, including any number of two-dimensional display units or any number of spatial display units.

In an embodiment, the system 100 is a PACS with display units 120-160 representing the display units of PACS. The computer unit 110 may represent equipment and components of a PACS system other than the display units. The computer unit 110 and display units 120-160 may be separate units or be part of a single unit. In the case of separate units, the display units 120-160 may be in electrical communication with the computer unit 110. The components of the system 100 may be single units, separate units, may be integrated in various forms, and may be implemented in hardware and/or in software.

In an embodiment, a display protocol may allow a user to view multiple three-dimensional volumetric medical images concurrently on spatial display units 150 and 160. The computer unit 110 may have computer software that may link the three-dimensional images for easier navigation and use. For example, the three-dimensional image displayed on spatial display unit 150 may be linked to the three-dimensional image displayed on spatial display unit 160. Allowing a user to view multiple three-dimensional images, or volume images, concurrently enables a user to easily compare the images. For example, a user may use a display protocol to instruct a volume image of a current study to be displayed on spatial display unit 150. A user may also use the display protocol to instruct a volume image of a comparison study to be displayed on spatial display unit 160. In such a manner, a current study may be easily compared to the comparison study, providing an efficient view for a user.

In operation of an embodiment, the volume image of a current study may be the image the user would like to examine. The volume image of a comparison study may be any image a user would like to compare to the current image. For example, the volume image of a current study may contain a set of organs from a current exam of patient A. A user may wish to view the same set of organs of patient A from a previous exam. A user may retrieve a comparison study from the computer unit 110, and display the comparison study on spatial display unit 160. In such an embodiment, the spatial display unit 160 is displaying an archived study. Additionally, the comparison study may be a volume image from a different patient. The above are only examples, and any volumetric medical images may be compared.

Once the display protocol has displayed the desired three-dimensional images in the appropriate locations, the computer unit 110 may link the volumetric medical images displayed on display units 150 and 160. In an embodiment of the invention, the display protocol links the volumetric medical images together so movement or rotation in one volume may drive similar movement or rotation in the other volumes. The angle of view of the volumetric image and object respresented may generally be kept consistent for the user. For example, if a current volumetric image of a patient's heart is displayed on spatial display unit 150 and a historical volumetric image of the patient's heart is displayed on spatial display unit 160, similar characteristics of the heart would occupy a similar space in each spatial display unit 150 and 160 respectively. The front of the heart as represented in spatial unit 150 would occupy the same space as the front of the heart has displayed on spatial display unit 160. As a user performs operations, such as rotate, flip, zoom, or other operations, on a first spatial image, the other spatial images alter their viewing characteristics to be consistent with the image controlled by the user.

In the embodiment of system 100, a user may select a three-dimensional image on display unit 150 or display unit 160 with a computer mouse, and use the computer mouse to rotate the image. The selected image may be the driver image. Rotation or movement in the driver image may drive rotation in the other three-dimensional image. For example, the user may select the current study on display unit 150 as the driver image. The user may then rotate or move the angle of view of the current study using the computer mouse. Because the display protocol has linked the comparison study on display unit 160, the comparison study may move or rotate to present an angle of view similar to the angle of view displayed for the current study. In such a manner, the user may view a similar angle of view for both the current study and the comparison study. Moreover, a user may manipulate an on screen pointer to point to a specific location on the driver image. The display protocol may then manipulate the pointer on an other image to point to a corresponding location. As a user moves the pointer in the driver image, the pointers in the other images correspondingly move to point to the same location. In such a manner, the user may be able to compare similar structures in multiple images more easily. The ability to link the volumetric medical images together increases the efficiency and accuracy of a user for diagnosis and treatment.

Figure 2:
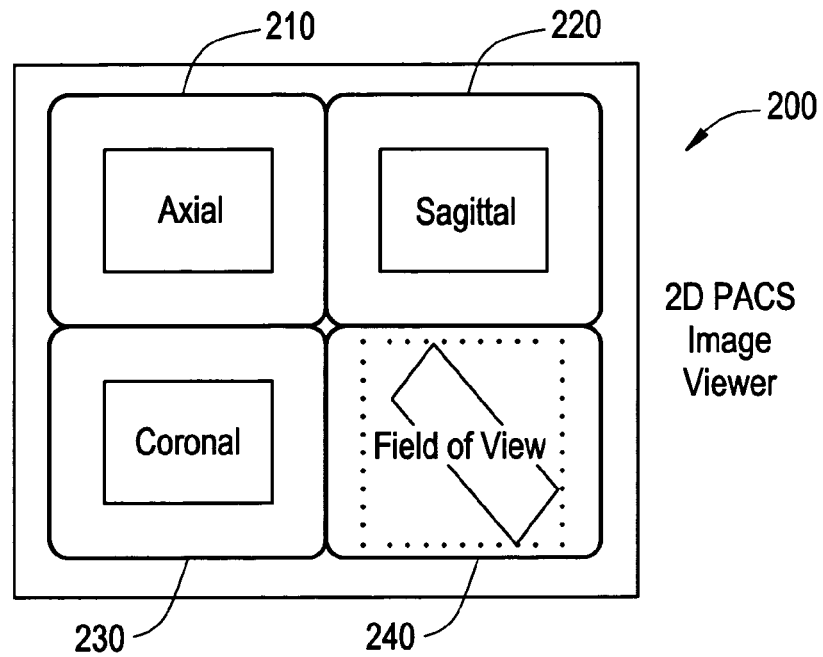
FIG. 2 illustrates a plurality of two-dimensional images that may be displayed on display units, such as display units as illustrated in FIG. 1, in accordance with an embodiment of the present invention.
Figure 3:
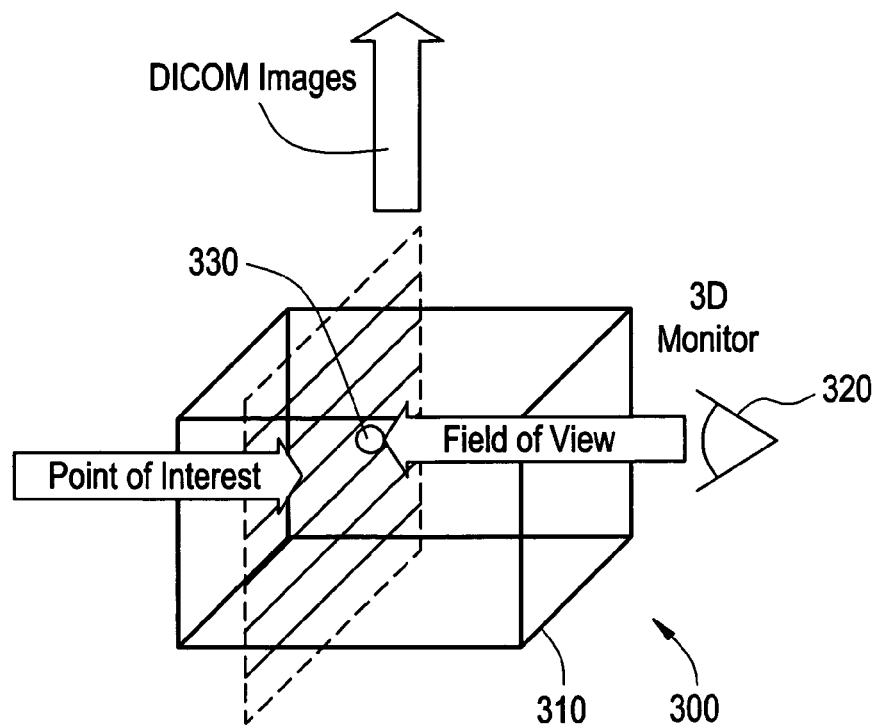
FIG. 3 illustrates a mapping of a three-dimensional image to two-dimensional space in accordance with an embodiment of the present invention.

In another embodiment of the present invention, two-dimensional images may be linked to the driver volumetric image. Accordingly, in the system 100, the two-dimensional images may be displayed on display units 120-140 and the three-dimensional images may be displayed on spatial display units 150 and 160. As the system 100 is one embodiment of the present invention, any number of display units may be used. In the embodiment discussed above, two volumetric data sets exist, the current data set is displayed on spatial display unit 150 and the comparison data set is displayed on spatial display unit 160. Both of these data sets have corresponding two-dimensional images. In an embodiment, a user may display the two dimensional images of the driver three-dimensional image by selecting a point of interest on the driver three-dimensional image. FIGS. 2 and 3 illustrate the concept of point-of-interest and the relationship between the two-dimensional display units 120-140 and three-dimensional spatial display units 150-160.

FIG. 2 illustrates a plurality of two-dimensional images 200 that may be displayed on display units 120, 130, or 140 in the embodiment of the system 100. FIG. 2 comprises four two-dimensional images, an axial image 210, a sagittal image 220, a coronal image 230, and an oblique image 240. Any combination of images 210-240 may be displayed on display units 120-140.

FIG. 3 illustrates a mapping 300 of a three-dimensional image to two-dimensional space. FIG. 3 comprises a three-dimensional model 310 that may be displayed on the three-dimensional display units 150 or 160 in FIG. 1. FIG. 3 also comprises a representation of a user's field of view 320 and a point of interest 330. The user's field of view represents the angle of view displayed by the three-dimensional monitors 150 or 160 after a user has manipulated the three dimensional images. As mentioned above, display unit 150 and display unit 160 may display a current and comparison exam respectively, and as the current and comparison exams are linked, the display unit 150 and display unit 160 should have a similar, if not the same field of view 320.

The point of interest 330 may be a point in the three-dimensional model 310 of particular interest to the user. A user may select a point of interest 330 using a computer mouse or other input device. Once a user selects a point of interest 330 on the three-dimensional model, the two-dimensional images 210-230 for the point of interest 330 may be displayed on the display units 120-140. If an oblique two-dimensional view exists for the selected point of interest, the oblique view 240 may also be displayed on display units 120-140. For example, if two dimensional images for the field of view oblique view 240 are available for a particular point of interest, the oblique view may also be displayed on one of the two dimensional monitors 120-140.

In an embodiment of the invention, a user may manipulate the parameters of three-dimensional images on display units 150 or 160 to reach a particular field of view 320. A user may then select a particular point of interest 330 on either display unit 150 or display unit 160. After the particular point of interest 330 is selected on one of the three-dimensional monitors, the axial 210, sagittal 220, and coronal 230 views for that particular point of interest from that particular study may be displayed on display units 120-140. For example, if a user selects the point of interest on the current study displayed on spatial display unit 150, the axial 210, sagittal 220, and coronal 230 views for the current exam are displayed on display units 120-140, respectively. If a user selects the point of interest on the historical or comparison study displayed on display unit 160, the axial 210, sagittal 220, and coronal 230 views for the historical or comparison study are displayed on display units 120-140, respectively. Accordingly, a user may drive a particular three-dimensional view 320, select a point of interest 330, and view both the three dimensional and two-dimensional images of the point of interest.

In an embodiment, a user may utilize the system 100 and associated components of FIGS. 200 and 300 to plan and review a surgical path. A surgical path may comprise the path of an instrument or incision a physician may make during surgery. A surgeon may wish to review the surgical path prior to surgery to make the intrusion into the patient's body as minimal as possible or to create a "blueprint" for the surgery. A review of the surgical path prior to or during surgery may make surgery more efficient and effective. Moreover, subsequent to surgery, a user may compare the surgical path over various periods of time. For example, a user may compare the surgical path before surgery and after surgery to monitor the level of disturbance created by the surgery. Also, a user may compare the surgical path at various times after surgery to monitor recovery.

FIG. 4 illustrates the embodiment of utilizing the system 100 and associated components of FIGS. 200 and 300 to plan and review a surgical path. FIG. 4 comprises two three-dimensional models 410 and 420 that may be displayed on the three-dimensional units 150 and 160 in FIG. 1. Model 410 illustrates a three-dimensional model that may represent a volumetric image from a historical study. Model 420 illustrates a three-dimensional model that may represent a volumetric image from a current study. Each three-dimensional model, 410 and 420, may be displayed on spatial display units 150 and 160. Each three-dimensional model, 410 and 420, shows a series of shaded ovals that represent a series of two-dimensional "snap-shots." Each two-dimensional snap-shot may represent an independent point of interest, and thus an independent set of two dimensional images. Accordingly, each snap-shot may have an associated axial, sagittal, and coronal view, as well as a possible oblique view. In such a manner, a user may step through a surgical path in both two and three dimensions.

A user may create a surgical path by taking a series of "snap-shots" though a volumetric image. The snap-shots may be created by varying the point of interest, the field of view, the zoom magnitude, the level of depth within an image, and other parameters available to the user. Once the user selects the appropriate parameters, the parameters may be captured and recorded as a frame. In the example shown in FIG. 4 for model 410, each shaded oval, for example ovals 411-417, represent a frame. As the three-dimensional image is linked to the two-dimensional images, each frame may represent a set of three-dimensional parameters and a set of two dimensional parameters. Accordingly, a user may capture a frame, for example frame 411, re-adjust the parameters of an image, and capture a new frame. When a frame is captured, the frame's parameters and location in the series are recorded. In the example shown in FIG. 4 for model 410, a user may capture frame 411, re-adjust the parameters of model 410, and capture frame 412. A user may repeat the process until the user is satisfied with the number of frames. In such a manner, a user may create a series of two and three-dimensional images that comprise a path through the anatomy of a patient.

Once the surgical path 411-417 has been created, a user may review the surgical path 411-417 during surgery as a guide to conducting the surgery. The surgical path may be reviewed in two or three-dimensions. For example, the surgeon may review the surgical path frame by frame in two-dimensional space. Additionally, the surgeon may review the surgical path in three-dimensional space. A review in three-dimensional space may include a review of the surgical path frame by frame or through an extrapolated view. The extrapolated view is aided by computer software that "fills in" the distance between frames so the three-dimensional review is illustrated smoothly, as if a video.

As mentioned above, FIG. 4 also illustrates model 420. Model 420 illustrates a first three-dimensional model that may represent a data set different from the data set as represented by model 410. For example, model 410 may represent a data set of a specific anatomical region imaged before surgery. Model 420 may represent a data set of the same anatomical region, but imaged after surgery. In such an embodiment, it may be useful for each image set to have the same surgical path. If the image sets have the same surgical path, a user may compare images of the same anatomical features of a patient, but at different points in time.

In an embodiment of the invention, a user may map a previously created surgical path to a new data set. In order to review a previously created surgical path in a new data set, the surgical path parameters may be mapped to the new data set. For example, in order to review the surgical path 411-417 of model 410 in the data set of model 420, the surgical path 411-417 may be mapped to create the surgical path 421-427. In an embodiment, the parameters of the individual frames of data set 410 are mapped to create similar frames in data set 420. For example, the parameters of frame 411 are mapped to create frame 421. The parameters of frame 412 are mapped to create frame 422. The process of mapping the parameters of a previous data set to a new data set may be repeated to create a similar surgical path in both data sets.

For example, model 410 may represent a historical study with a surgical path 411-417 generated prior to surgery. Model 420 may represent a current data set acquired after surgery. The surgical path 411-417 in the historical study may be mapped to create the surgical path 421-427 in the current study. As the two surgical paths 411-417 and 421-427 have similar viewing parameters, the images of the surgical paths should illustrate the same anatomical structures at different points in time. A user may display the surgical path 411-417 on display unit 150 and surgical path 421-427 on display unit 160. The associated two-dimensional images with each surgical path may be displayed on the two-dimensional display units 120-140. As the three-dimensional images may be linked, movement through one of the surgical paths may create associated movement through the other surgical path. For example, as the historical study 410 may be linked to the current study 420, the display of structures in each study may generally be consistent. The display of each study may be adjusted based on what is displayed in the other study.

FIG. 5 illustrates a method 500 for utilizing two and three dimensional images to review a surgical path in accordance with an embodiment of the present invention. At step 510, a user may manipulate the display parameters of a three-dimensional image displayed on a display unit, including selecting a point of interest. For example, a user may use a keyboard, mouse, trackball or other input device to alter the display parameters. The display parameters may include the angle of view, point of interest, depth of view, zoom magnification, or other viewing parameters. At step 520, the display parameters of the three-dimensional image may be recorded and the two dimensional images recorded as a frame in a surgical path. In an embodiment, a surgical path may correspond to series 411-417, as displayed in FIG. 4. Additionally, a frame in the surgical path may correspond to one of the elements 411-417. At step 530, the steps of 510 and 520 are repeated until the surgical path is of desired length. The desired length of the surgical path may be determined by a user.

At step 540, the display parameters of the surgical path from a first data set may be mapped to a second data set. By mapping the display parameters of the first data set to the second data set, the second data set may have a substantially similar surgical path as the first data set. For example, in order to review the surgical path 411-417 of model 410 in the data set of model 420, the surgical path 411-417 may be mapped to create the surgical path 421-427. In an embodiment, the parameters of the individual frames of data set 410 are mapped to create similar frames in data set 420. For example, the parameters of frame 411 are mapped to create frame 421. The parameters of frame 412 are mapped to create frame 422. The process of mapping the parameters of a previous data set to a new data set may be repeated to create a similar surgical path in both data sets.

At step 550, the surgical path of the first data set and the surgical path of the second data set may be displayed on spatial display units, such as display units 150 and 160. For example, if the first data set is a historical data set prior to surgery, the surgical path of the historical data set illustrates the condition of the patient prior to surgery. A user may map the surgical path of the historical data set to a current data set, so the historical data set and current data set have substantially similar surgical paths. Accordingly, a user may compare the anatomical structures along a surgical path before and after surgery.

The system and method described above may be carried out as part of a computer-readable storage medium including a set of instructions for a computer. The set of instructions includes a manipulation routine to manipulate the display parameters of a three-dimensional image displayed on a display unit, including selecting a point of interest. The set of instructions also includes a recordation routine to record the display parameters of the three-dimensional image and the two dimensional image as a frame in a surgical path. The set of instructions also includes a repeat routine to repeat the manipulation routine and the recordation routine until the surgical path is of desired length. The set of instructions also includes a mapping routine to map the display parameters of the surgical path from a first data set to a second data set. The set of instructions also includes a display routine to display the surgical path of the first data set and the surgical path of the second data set.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for using medical images to review a surgical path, said method comprising:
   manipulating the display parameters of a first three-dimensional data set displayed on a spatial display unit;
   recording the display parameters of said first three-dimensional data set, and recording the corresponding two-dimensional images, as a frame in a surgical path, wherein said surgical path represents a surgical blueprint that comprises a path of an instrument or incision that may be made during surgery;
   repeating the above steps of manipulating and recording until said surgical path is of the desired duration, said desired duration being determined by a user;
   mapping the display parameters of said first three-dimensional data set to a second three-dimensional data set; and
   displaying said surgical path of said first three-dimensional data set and a surgical path of said second three-dimensional data set on the spatial display unit.

2. The method of claim 1, wherein said surgical path of said first three-dimensional data set is linked to the surgical path of said second three-dimensional data set.

3. The method of claim 1, wherein an axial, sagittal, and coronal view is recorded for each frame.

4. The method of claim 1, wherein an oblique view is recorded for each frame.

5. The method of claim 1, wherein said first three-dimensional data set is a historical data set and said second three-dimensional data set is a current data set.

6. The method of claim 1, wherein an axial, sagittal, and coronal view is recorded for the point of interest for each frame.

7. A computer-readable storage medium including a set of instructions for a computer, the set of instructions comprising:
   a manipulation routine for manipulating the display parameters of a first three-dimensional data set displayed on a spatial display unit;
   a recordation routine for recording the display parameters of said first three-dimensional data set, and recording the corresponding two-dimensional images, as a frame in a surgical path, wherein said surgical path represents a surgical blueprint that comprises a path of an instrument or incision that may be made during surgery;
   a repeat routine for repeating the above steps of manipulating and recording until said surgical path is of the desired duration, said desired duration being determined by a user;
   a mapping routine for mapping the display parameters of said first three-dimensional data set to a second three-dimensional data set; and
   a display routine for displaying said surgical path of said first three-dimensional data set and a surgical path of said second three-dimensional data set on the spatial display unit.

8. The computer instructions of claim 7, wherein said surgical path of said first three-dimensional data set is linked to the surgical path of said second three-dimensional data set.

9. The computer instructions of claim 7, wherein an axial, sagittal, and coronal view is recorded for each frame.

10. The computer instructions of claim 7, wherein an oblique view is recorded for each frame.

11. The computer instructions of claim 7, wherein said first three-dimensional data set is a historical data set and said second three-dimensional data set is a current data set.

12. The computer instructions of claim 7, wherein an axial, sagittal, and coronal view is recorded for the point of interest for each frame.

* * * * *